(12) United States Patent
Molloi

(10) Patent No.: US 10,201,321 B2
(45) Date of Patent: Feb. 12, 2019

(54) LOW-DOSE CT PERFUSION TECHNIQUE

(71) Applicant: The Regents of the University of California, Oakland, CA (US)

(72) Inventor: Sabee Molloi, Laguna Beach, CA (US)

(73) Assignee: The Regents of the University of California, Oakland, CA (US)

( * ) Notice: Subject to any disclaimer, the term of this patent is extended or adjusted under 35 U.S.C. 154(b) by 152 days.

(21) Appl. No.: 15/206,075

(22) Filed: Jul. 8, 2016

(65) Prior Publication Data

US 2017/0007195 A1    Jan. 12, 2017

Related U.S. Application Data

(60) Provisional application No. 62/190,904, filed on Jul. 10, 2015.

(51) Int. Cl.
*G06K 9/00* (2006.01)
*A61B 6/00* (2006.01)
*A61B 6/03* (2006.01)

(52) U.S. Cl.
CPC .............. *A61B 6/507* (2013.01); *A61B 6/032* (2013.01); *A61B 6/501* (2013.01); *A61B 6/503* (2013.01); *A61B 6/5217* (2013.01); *A61B 6/583* (2013.01)

(58) Field of Classification Search
None
See application file for complete search history.

(56) References Cited

U.S. PATENT DOCUMENTS

| | | | | |
|---|---|---|---|---|
| 2012/0136243 A1* | 5/2012 | Boese | ................. | A61B 5/0275 600/425 |
| 2013/0211247 A1* | 8/2013 | Kalafut | ............... | G06F 19/3437 600/432 |
| 2014/0163403 A1* | 6/2014 | Lenox | .................... | A61B 5/026 600/504 |
| 2015/0038860 A1* | 2/2015 | Fonte | ...................... | A61B 6/50 600/505 |

* cited by examiner

*Primary Examiner* — Weiwen Yang
(74) *Attorney, Agent, or Firm* — Knobbe Martens Olson & Bear LLP

(57) ABSTRACT

Methods and apparatuses are disclosed for quantifying regional organ perfusion with low radiation dose using whole-organ CT in a patient comprising obtaining a computed tomography scan of the patient and determining perfusion of the organ using a first-pass analysis method in conjunction with conservation of mass for perfusion measurement.

17 Claims, 13 Drawing Sheets
(12 of 13 Drawing Sheet(s) Filed in Color)

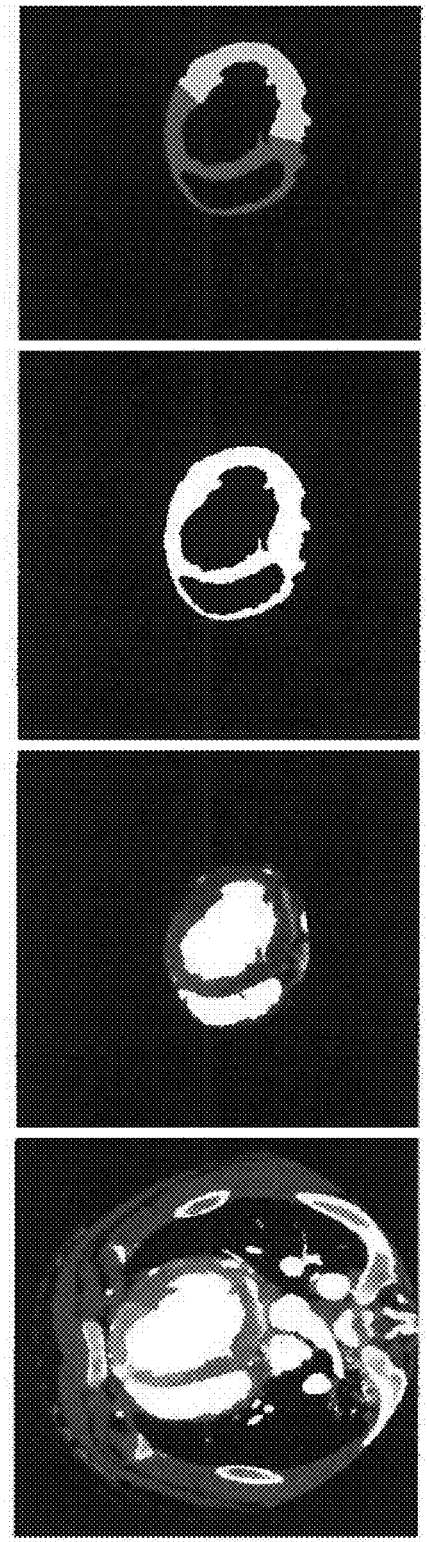

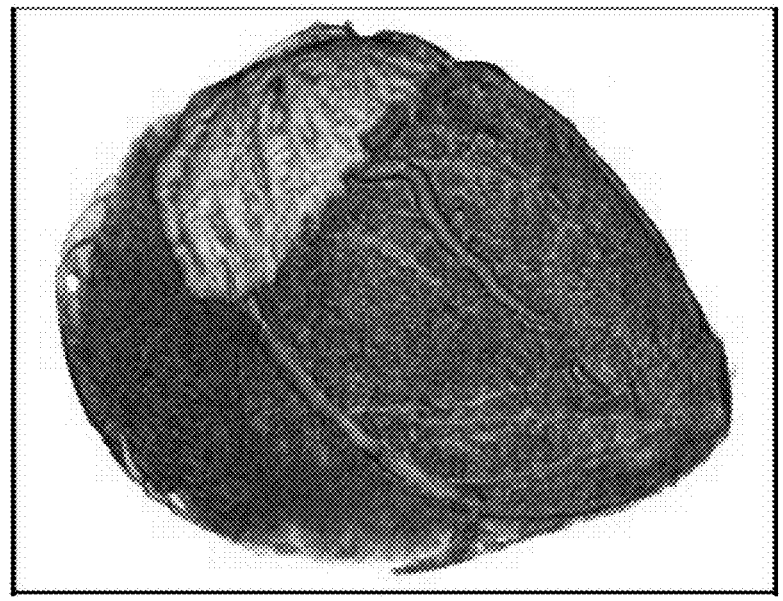
FIG. 14E
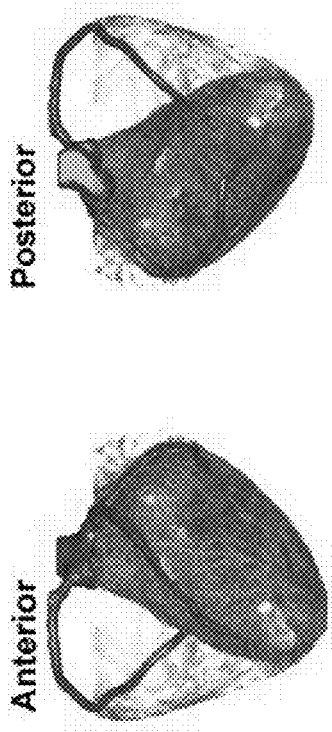
FIG. 14B
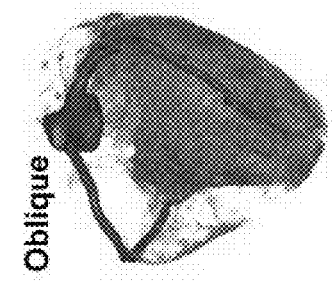
FIG. 14D
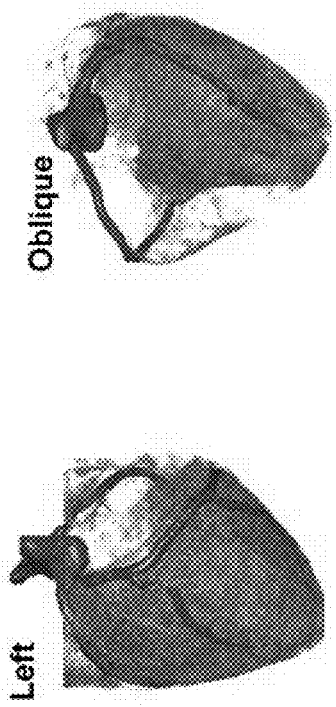
FIG. 14A
FIG. 14C

LOW-DOSE CT PERFUSION TECHNIQUE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to systems and methods for computed tomography (CT) angiography procedures, and more particularly, to a system and method for a low dose CT perfusion technique for routine functional assessment of coronary artery disease.

Description of the Related Art

Coronary heart disease is the leading cause of death and morbidity worldwide. Currently the most-used noninvasive method for visualizing coronary atherosclerosis is coronary computed tomographic (CT) angiography. Although the method's image quality has improved greatly over the last decade, previous CT angiography studies have often overestimated stenosis severity. Furthermore, it is difficult to reliably assess the severity of a stenosis in the presence of coronary artery calcification. It is also difficult to determine stenosis severity when assessing intermediate coronary lesions (30%-70% diameter stenosis), where angiography has only limited ability to distinguish ischemia-producing from non-ischemia-producing obstructions.

Conventional semi-quantitative myocardial perfusion imaging, such as single-photon emission computed tomography (SPECT), is commonly used for functional assessment of these coronary lesions. However, these techniques only estimate relative perfusion, which is limited in its ability to identify the extent of multivessel coronary artery disease burden and balanced 3-vessel coronary artery disease. Dynamic myocardial perfusion in absolute terms (ml/min/g) is possible using positron emission tomography (PET), which extends the scope of conventional semi-quantitative myocardial perfusion imaging. However, myocardial perfusion with PET is limited by access to necessary radiolabeled tracers, radiation dose, and cost.

CT perfusion techniques to provide functional assessment of stenosis severity. However, widespread clinical implementation of such techniques has been hampered by the fact that these techniques generally underestimate the actual myocardial perfusion and deliver a very high radiation dose to the patient.

SUMMARY

Embodiments of the present disclosure relate to a low dose CT Perfusion technique that can assess both anatomical and physiological consequences of coronary artery disease in a single, noninvasive test. In some embodiments, the disclosed low dose CT Perfusion technique can assess the percent stenosis that has occurred within the coronary artery. In some examples, the disclosed low dose CT Perfusion technique can assess the change in perfusion within the coronary artery as a result of coronary artery disease.

Disclosed herein is a method for measuring tissue perfusion using a low-dose CT Perfusion technique to accurately quantify regional perfusion using a first-pass analysis method and conservation of mass principles. The disclosed method can be used to quantify the effects of both coronary artery stenosis and microvascular disease on myocardial perfusion. The disclosed method utilizes a single noninvasive test that can assess both anatomical and physiological consequences of a coronary artery stenosis or microvascular disease while exposing the patient to lower radiation doses as compared to traditional methods.

In some embodiments, a method of quantifying regional organ perfusion with low radiation dose using whole-organ CT in a patient is disclosed. In some embodiments, the method comprises: obtaining a computed tomography scan of the patient; determining perfusion of the organ using a first-pass analysis method in conjunction with conservation of mass for perfusion measurement. In some embodiments, the conservation of mass measurement comprises determining the entire organ perfusion volume. In some embodiments, the conservation of mass measurement comprises determining a large sub-volume of the organ. In some embodiments, the conservation of mass measurement can be modeled as a compartment with a unique organ entrance and organ exit vessel. In some embodiments, the perfusion volume measurement comprises determining the amount of iodinated blood entering the vascular compartment within a specific time interval.

In some embodiments, the method further comprises applying the formula:

$$P = \frac{Q}{M} = \frac{1}{MC_{ave}}\left(\frac{\Delta V}{\Delta t}\right)_{ave}$$

wherein P is the calculated perfusion (ml/min/g), Q is the calculated blood flow (ml/min), M is the tissue mass (g) calculated using the total volume of tissue in the compartment and the known physical density of tissue, $\Delta V/\Delta t$ is the rate of change in iodinated blood volume in the perfusion volume per unit time, and $C_{ave}$ is the average iodine concentration of the incoming blood at the time of measurement, derived from the arterial input for the tissue compartment.

In some embodiments, the method comprises calculating global perfusion by using the entire segmented myocardium as the perfusion volume of interest. In some embodiments, the method comprises calculating perfusion using a single volume of interest. In some embodiments, the organ is at least one of: a heart, a brain, a lung, a kidney, and a liver. In some embodiments, the scan is performed using 2 volume scans. In some embodiments, the scan is performed using at least 3 volume scans. In some embodiments, the scan is performed using 5 volume scans. In some embodiments, CT angiography data is obtained simultaneously. In some embodiments, the scan is performed using 0.5-5 mSv. In some embodiments, the scan is performed using 2.5 mSv. In some embodiments, the scan is performed using less than 5 mSv. In some embodiments, the method further comprises measuring vessel-specific perfusion by performing vessel centerline extraction and perfusion bed assignment.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 6A-6D illustrate an example of the image segmentation process.

FIGS. 14A-14E illustrate 3D overlays of CT angiography and CT perfusion, showing anterior, posterior, left and oblique views, with an additional tissue overlay.

DETAILED DESCRIPTION

Figure 1:
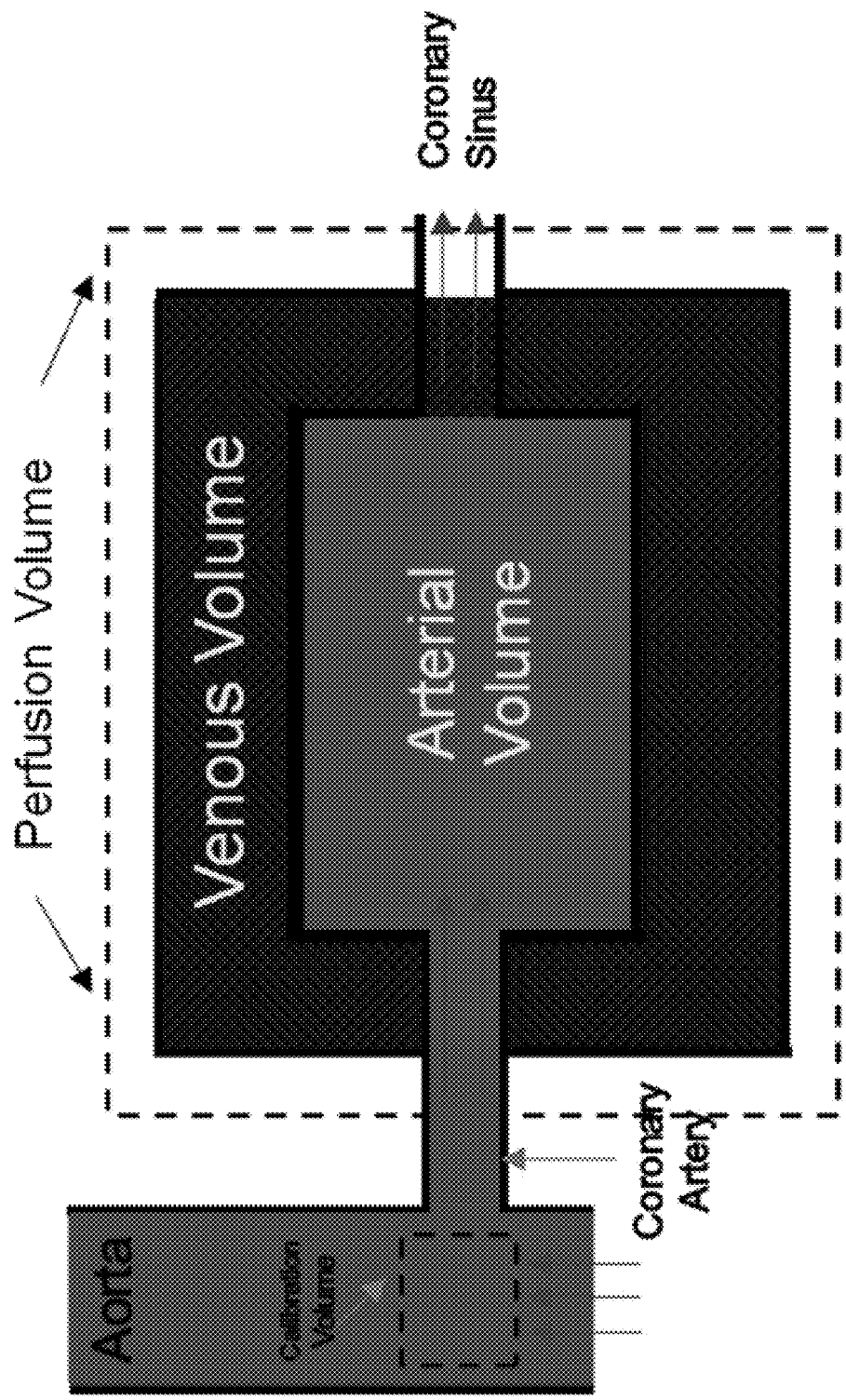
FIG. 1 illustrates a single compartment model used in first-pass analysis to represent the entire myocardial perfusion volume, or a large sub-volume, with a unique entrance and exit vessel.

Despite the well-recognized discrepancies between a stenosis's angiographic and functional significance, coronary angiography is still often used as the principal diagnostic tool to determine whether to perform percutaneous coronary intervention. Fractional flow reserve (FFR), a percentage of theoretically normal flow transmitted across a stenotic artery is a method to provide a physiological measure of coronary stenosis. Although previous studies have shown that FFR can be used to improve clinical outcomes and reduce the risk of a cardiac event or death, its application is invasive.

Some noninvasive imaging modalities, such as stress echocardiography, cardiac magnetic resonance, and myocardial perfusion scintigraphy, can be used to perform physiological assessment. These modalities identify individuals with severe stenosis by using wall motion abnormalities or regional differences in coronary flow reserve (CFR) as a surrogate for ischemia. These imaging techniques are robust for detecting patients with ischemia; however, they have poor discrimination of the specific coronary vessels that are responsible for ischemia. For instance, when using an FFR standard for vessel-specific ischemia, myocardial perfusion scintigraphy identifies ischemic territories correctly less than 50% of the time, underestimating and overestimating in 36% and 22% of cases respectively.

Traditional noninvasive CT angiography also lacks sufficient accuracy and often leads to overestimation of stenosis severity. Furthermore, it has been reported that CT angiography identifies coronary lesions as a severe cause of ischemia less than one-half of the time. This finding has led to concerns that widespread CT angiography application may result in unnecessary invasive coronary angiography. While recent advances in PET and MRI imaging modalities have allowed the use of perfusion measurement, and also regional indices and quantification of blood flow inhomogeneity, the complexity and cost associated with such modalities has hampered widespread implementation of these techniques for routine noninvasive diagnosis of coronary artery disease.

CT myocardial perfusion imaging can be used to determine a stenosis's hemodynamic significance. It is possible to acquire either a static CT perfusion scan, where the relative uptake of contrast material in the myocardium is assessed from a single volume scan, or a dynamic CT perfusion scan, where approximately 15-30 volume scans are acquired as contrast enters the myocardium. While the dynamic CT perfusion approach has the potential to provide quantitative myocardial perfusion information, existing techniques underestimate the actual myocardial perfusion and further require a large number of volume scans, and therefore, a large radiation dose.

These techniques, such as the maximum slope model, monitor the enhancement of the aorta or left ventricle and a number of small regions of myocardium over time. Curve-fitting is performed on these time-series data, and myocardial blood flow is calculated using parameters from the model fits. While such measurement techniques show varying degrees of correlation to gold standard microsphere myocardial blood flow measurements, they also show some disagreement amongst each other and overall they tend to underestimate myocardial blood flow.

The problem of underestimation stems fundamentally from the rapid transit time of contrast material throughout the myocardium. Specifically, these first-pass techniques operate under the assumption that no contrast material leaves the myocardial volume of interest (VOI) during the measurement period. However, these techniques are inherently subject to contrast material loss during measurement. These techniques generally make the measurements using a number of small VOIs is that are typically 1-1.5 $cm^2$ in cross section and 0.3 cm thick, over many cardiac cycles, thus resulting in contrast material loss from those VOIs, especially at hyperemia. This problem of contrast loss is only compounded by the fact that the smaller the VOI, the shorter the effective transit time of blood throughout that VOI, and the more blood flow is underestimated.

This problem can be addressed by increasing the size of the sampled region to a much larger VOI that could encompass the entire perfusion bed of an artery or a major arterial branch. Unfortunately, most clinical CT systems are limited in their Z-axis coverage, reducing the myocardial volume that can actually be sampled within one cardiac cycle. As a result, existing CT perfusion techniques have had minimal success in accurately quantifying absolute myocardial perfusion, primarily due to technological limitations.

Disclosed Method for Low-Dose CT Perfusion Technique

Recent advances in CT technology, specifically increased detector Z-axis coverage (~16 cm) and increased temporal resolution, have introduced the ability to image a whole organ in a single gantry rotation within a fraction of a cardiac cycle has the potential to solve the transit time problems from which many first-pass distribution techniques currently suffer. Wide-detector CT allows a whole organ, such as a heart, to be imaged in a single acquisition, effectively lengthening the imaging window as transit time at maximum hyperemia i.e., the time between blood entering the coronary arteries and exiting via the coronary sinus, generally ranges from 3 to 5 seconds. As a result, the complicated problems of myocardial contrast dynamics and absolute myocardial perfusion quantification can be distilled into conservation of mass concepts.

Disclosed herein is a low-dose CT Perfusion technique capable of measuring absolute myocardial perfusion in a single non-invasive procedure. While this technique can be performed using standard invasive coronary angiography procedures by making measurements in an arterial tree perfusion bed before contrast exits through the venous system, noninvasive implementation of this technique is possible using currently available whole-organ CT scanners capable of scanning the whole heart within a cardiac cycle.

The disclosed CT perfusion technique for coronary artery disease assessment can have a number of advantages over the existing technology. In some embodiments, the disclosed CT perfusion technique can measure dynamic myocardial perfusion, making it possible to distinguish between normal and diseased perfusion beds on a vessel-specific basis. In some embodiments, the disclosed CT perfusion technique can substantially reduce the radiation dose to the patient. In some embodiments, the disclosed CT perfusion technique can allow the simultaneous acquisition of CT angiography and perfusion data.

In some embodiments, the disclosed technique can provide vessel specific perfusion measurement. Traditional techniques typically calculate perfusion in each of 17 standard segments of the myocardium. However, individually defined territories deviate from standard territories in 52% of patients. Accordingly, the disclosed technique calculates the myocardial mass at risk distal to a stenosis, which can be used to provide estimations concerning the myocardial mass distal to a stenosis on a vessel-specific basis. In some embodiments, this technique can use an assignment algorithm based on minimum energy consumption, to assign each voxel within the myocardium to the closest coronary arterial tree. Thus, the disclosed technique provides a quantitative vessel-specific perfusion bed assignment on a voxel by voxel basis, thereby addressing a limitation of existing clinical techniques which require two different tests for anatomic (CT angiography) and physiological assessment (PET) for a qualitative assessment of the standard 17 segments of myocardium.

In some embodiment, the disclosed technique can be used to quantify the effects of both coronary artery stenosis and microvascular disease on myocardial perfusion. This non-invasive CT perfusion technique can provide both anatomical and physiological information from a single coronary low-dose CT perfusion examination. In some embodiments, this technique can quantify myocardial perfusion and diagnose vessel-specific ischemia using as few as two volume scans. Conversely, traditional CT Perfusion techniques require as many as 15-30 volume scans, exposing patients to radiation doses as high as 10-15 mSv. Since the method disclosed herein can be used with fewer volume scans than traditional CT perfusion techniques, the radiation dose can be substantially reduced. In some embodiments, the total radiation dose is less than 2 mSv.

In some embodiments, the technique allows the simultaneous acquisition of CT angiography and perfusion data. In some embodiments, the technique uses only a single contrast injection and two volume scans. Thus, not only is the total radiation dose reduced, but the need to make two separate contrast injections is eliminated. Therefore, anatomical and physiological information can be integrated into a single low-dose scan protocol. This is particularly important for patients with renal dysfunction.

Accordingly, the technique described herein represents a significant advance over existing techniques by reducing the number of volume scans required, reducing the total radiation dose, allowing for the simultaneous acquisition of CT angiography and perfusion data, and providing vessel specific perfusion measurement.

In some embodiments, the technique utilizes a first-pass analysis method to measure tissue perfusion, and operates using wide-detector CT technology and the principles of conservation of mass. Specifically, the entire myocardial perfusion volume, or a large sub-volume, can be modeled as a compartment with a unique entrance and exit vessel, as shown in FIG. 1. The model does not require any assumptions regarding the vascular compartment's internal structure or the nature of the exit conduits. To measure blood flow, the model can determine the volume of iodinated blood entering the vascular compartment within a specific time interval. Hence, the volume, V(t), of iodinated blood within such a vascular compartment may be described by a flow-concentration product integral having separate terms for the inflow and outflow:

$$V(t) = \int_0^t Q_i(t) C_i(t) dt - \int_{t_{min}}^t Q_o(t) C_o(t) dt \quad (1).$$

where Qi(t) and $Q_o$(t) are the incoming and outgoing blood flow rates, and Ci(t) and $C_o$(t) are the incoming and outgoing concentrations of contrast agent in the iodinated blood, respectively. The term $t_{min}$ denotes the minimum transit time of blood throughout the compartment, from entrance to exit. The transit time through the coronary vascular volume can be approximately 3-5 seconds; therefore, if the CT measurement is performed before the iodinated blood begins to exit the vascular volume, Eq. 1 simplifies to:

$$V(t) = \int_0^{t < t_{min}} Q_i(t) C_i(t) dt \quad (2)$$

Assuming (1) the mean blood flow is relatively constant, and (2) the input iodine concentration is known at the time of measurement, Eq. 2 becomes:

$$V(t) = Q \int_0^{t < t_{min}} C_i(t) dt \quad (3)$$

Using the second fundamental theorem of calculus, integrating from t to t+Δt, and dividing by Δt, Eq. 3 becomes:

$$\frac{1}{\Delta t} \int_t^{t+\Delta t} \frac{\Delta V}{\Delta t} dt = Q \frac{1}{\Delta t} \int_t^{t+\Delta t} C_{in} dt \quad (4)$$

Given the definition of the average value of a function and rearranging Eq. 4, the final mathematical form of the disclosed first pass analysis technique is:

$$Q = \frac{1}{C_{ave}} \left( \frac{\Delta V}{\Delta t} \right)_{ave} \quad (5)$$

where Q is the calculated blood flow, $$\frac{\Delta V}{\Delta t}$$

is the rate of change in iodinated blood volume in the vascular compartment per unit time, and $C_{ave}$ is the average iodine concentration of the incoming blood at the time of measurement, derived from the aorta or left ventricle. It is possible to calculate ΔV using the change in integrated Hounsfield units HU within the time interval of Δt. The integrated HU within the calibration VOI can be used to estimate $C_{ave}$ (HU/ml).

The volume of the perfusion bed can be converted to myocardial mass and the myocardial perfusion calculated (ml/min/g). Ultimately, the disclosed technique of myocardial perfusion is advantageous, not only because it extends the transit time window, but also because of its ability to quantify the absolute volume of iodinated blood that has entered the vascular compartment of interest, over a time interval Δt before $t_{min}$.

Thus, the present technique eliminates the need to acquire multiple volume scans over many cardiac cycles, which is a requirement of most currently available dynamic CT perfusion techniques. It also dramatically reduces the radiation burden of dynamic CT perfusion.

In some embodiments, all CT volume scans can be registered to a single coordinate system. In some embodiments, the image with the most contrast in each series can be selected as a reference, and GPU based affine and deformable registration can be applied to each subsequent CT image to minimize differences with the reference image. In some embodiments, the registration metric is based on normalized gradient fields, as opposed to image Hounsfield values due to the flow of contrast material.

In some embodiments, the registered images can be used to form a maximum intensity projection (MIP) image. The MIP image can be used as input for a twostep, semi-automatic segmentation algorithm. The first step can separate the heart region from the chest wall and lung region using user-defined input for several slices. The second step can separate the myocardium from the ventricles and atria in the MIP image by using optimally selected thresholds. This myocardium-only image can be used to create a binary mask which can be used as input into subsequent image processing steps. FIGS. 6A-D show an example of the image segmentation process.

Figure 7:
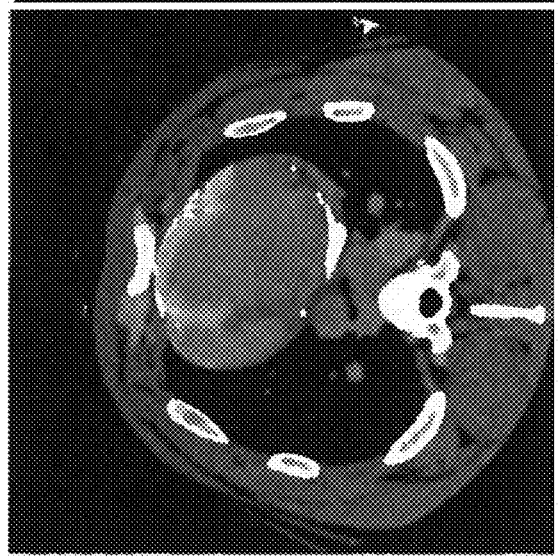
FIG. 7 illustrates an example of the LAD perfusion bed enhancement following direct contrast injection.

In some embodiments, CT volume scans can be transferred to a workstation, and the centerlines of the LAD, LCX, and RCA can be extracted to facilitate perfusion bed assignment. In some embodiments, centerlines can be extracted down to the smallest possible vessel diameter. FIG. 7 shows an example of the vessel centerline extraction process.

Figure 8:
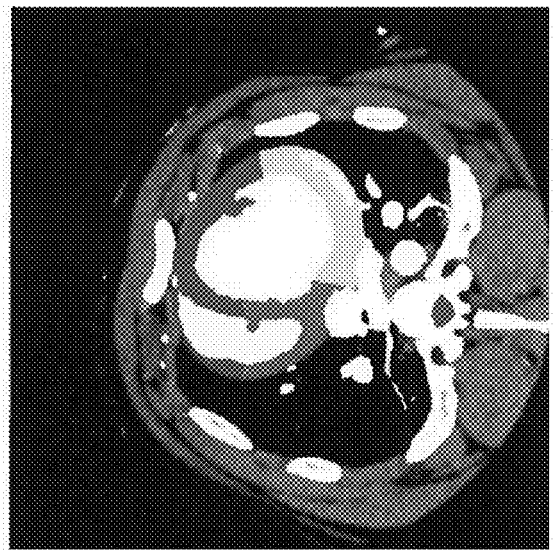
FIG. 8 illustrates the corresponding assigned LAD (red), LCX (green) and RCA (yellow) perfusion beds.

In some embodiments, the segmented myocardium mask and the extracted coronary vessels can be input into a suitable perfusion bed assignment algorithm using a minimum energy principle to determine three distinct perfusion beds for LAD, LCX and RCA. In some embodiments, the output of the bed assignment algorithm produces an image mask for each of the LAD, LCX and RCA perfusion beds (as shown in FIG. 7). FIG. 8 shows an example of the extracted coronary arteries and the assigned perfusion beds.

Figure 10:
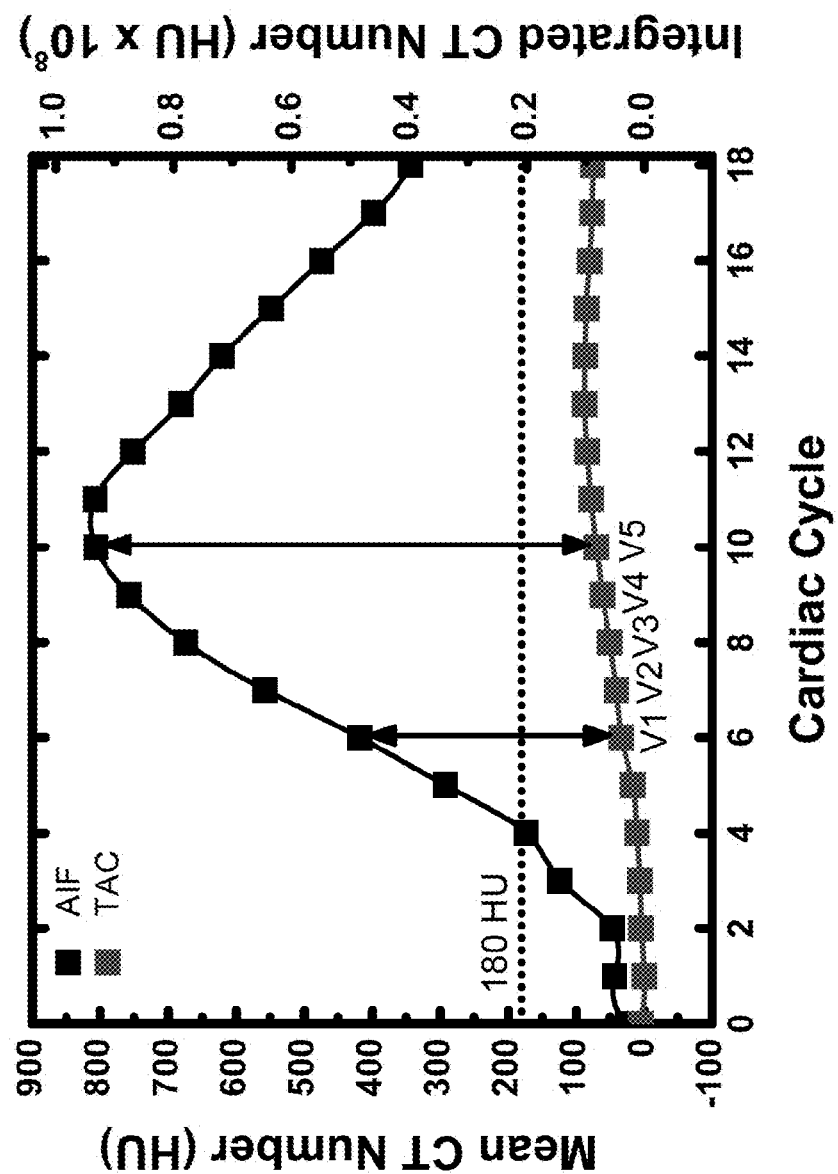
FIG. 10 illustrates examples of an AIF and myocardial TAC highlighting the volume scans used for perfusion calculations.

In some embodiments, the LAD, LCX and RCA perfusion bed masks can be used as VOIs to create three vessel-specific TACs to calculate perfusion. In some embodiments, an AIF may also be created using a VOI in the ascending aorta. FIG. 10 shows examples of an AIF and myocardial TAC highlighting the volume scans used for perfusion calculations. Similar to the phantom studies above, the maximum of the AIF was used as the arterial input concentration ($C_{ave}$ in Eq. 5) and perfusion was calculated using different number of volume scans. In some embodiments, the perfusion calculation can be based on two ($V_1$ and $V_5$), three ($V_1$, $V_3$ and $V_5$), and five ($V_1$-$V_5$) volume scans.

In some embodiments, the radiation dose can be further reduced by dose reduction techniques including mA modulation, and iterative reconstruction techniques. In some embodiments of the present technique, a CT angiography image ($V_5$) can also be generated. The radiation dose for the other volume scan ($V_1$) can be substantially reduced, due to the fact that this image is only used for perfusion measurement, and because the measurements are done using a relatively large VOI with many integrated voxels and the results are not very sensitive to quantum noise. In some embodiments, the radiation dose for the disclosed technique can approximate the dose that is currently used for just CT angiography.

In some embodiments, the vessel centerline extraction can take approximately 20 minutes. In some embodiments, the remaining steps can be fully- or semi-automated. In some embodiments, the entire time required for the disclosed CT perfusion calculation can be less than 30 minutes.

In some embodiments, the present CT perfusion technique can be applied to other organs such as brain, lungs and kidneys.

Accordingly, the technique described herein represents a significant advance over existing techniques by reducing the number of volume scans required, reducing the total radiation dose, allowing for the simultaneous acquisition of CT angiography and perfusion data, and providing vessel specific perfusion measurement.

Any structure, feature, or step in any embodiment can be used in place of, or in addition to, any structure, feature, or step in any other embodiment, or omitted. This disclosure contemplates all combinations of features from the various disclosed embodiments. No feature, structure, or step is essential or indispensable.

EXAMPLES

Example 1

Figure 2A:
FIG. 2A illustrates an embodiment of a cardiac phantom inside an anthropomorphic thorax.
Figure 2B:
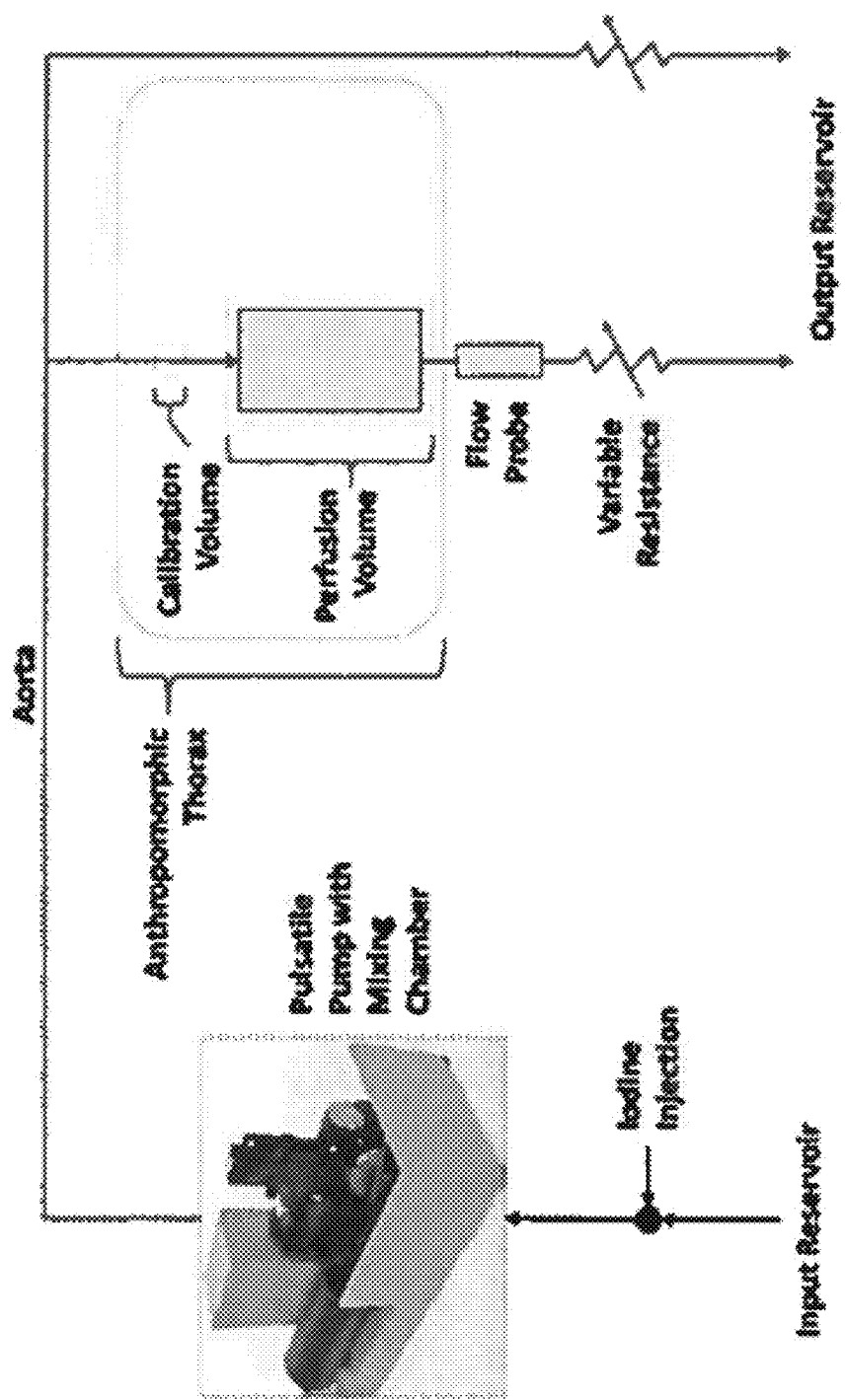
FIG. 2B illustrates a schematic diagram of the cardiac perfusion phantom comprising an input reservoir, pulsatile pump with a mixing chamber, myocardial perfusion volume, transit time flow probe, and output reservoir.
Figure 3B:
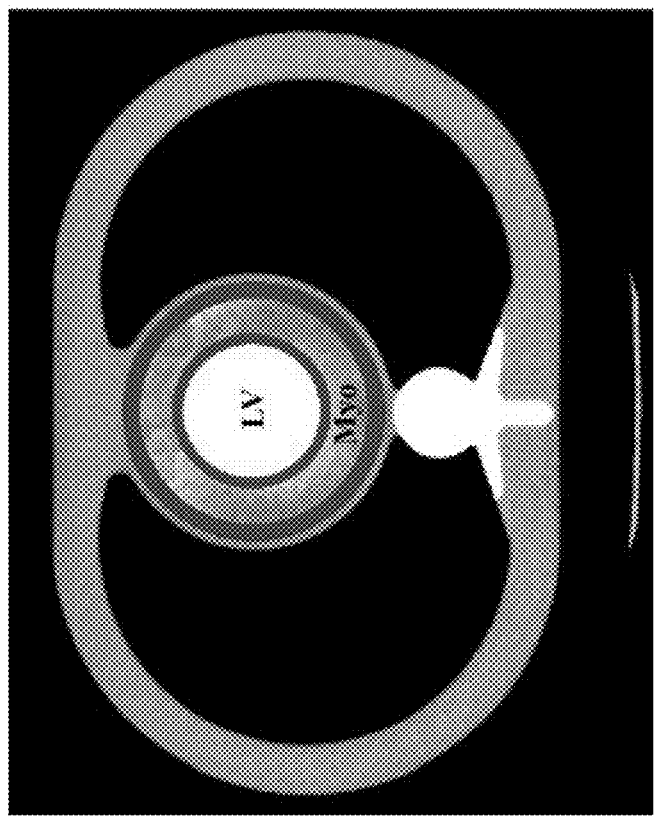
FIGS. 3A and 3B illustrate example CT images of the phantom, before and after contrast injection.
Figure 3A:
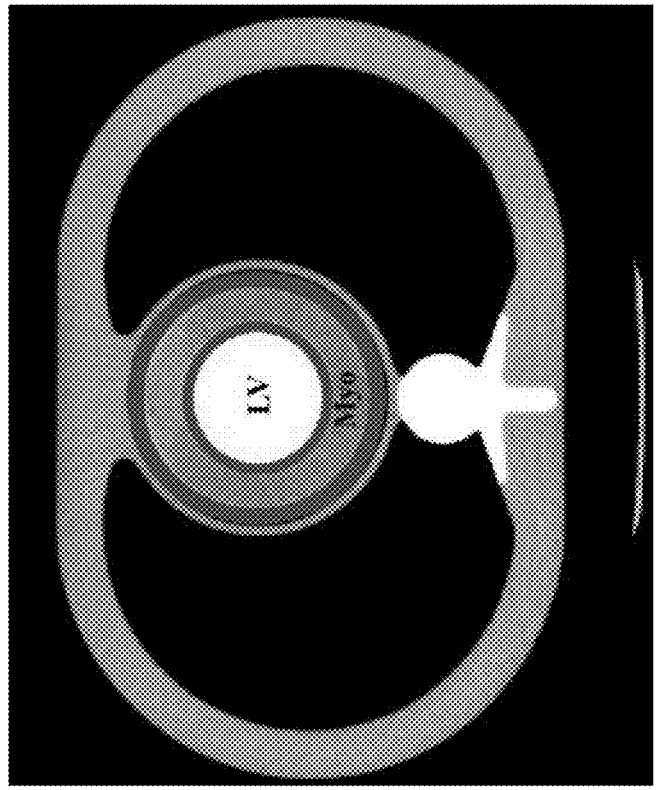
Figure 4:
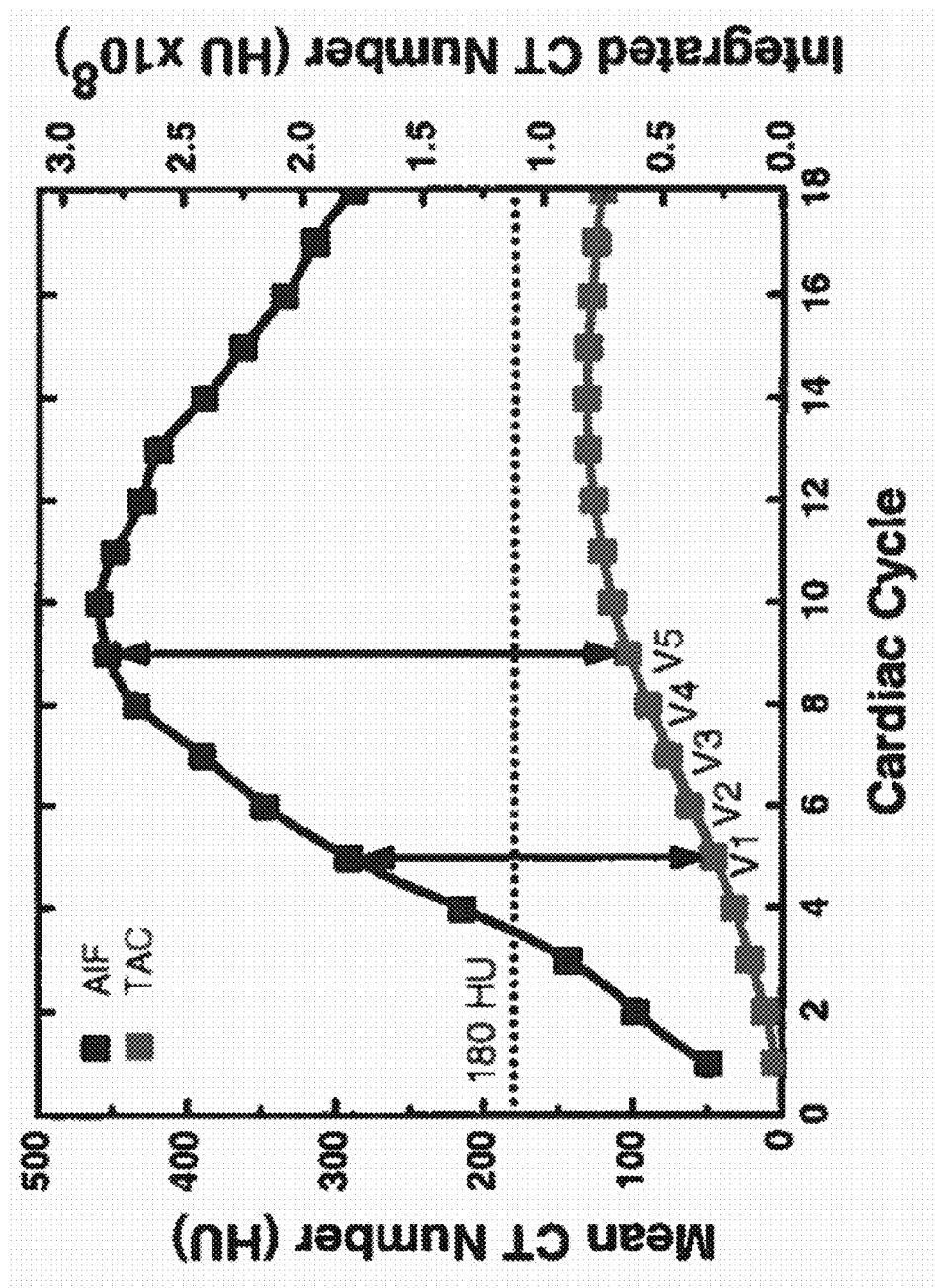
FIG. 4 illustrates an example arterial input function (AIF) and corresponding myocardial tissue time attenuation curve (TAC) showing the five volume scans ($v_1$-$v_5$) used for FPA perfusion calculations.

A cardiac phantom was constructed as shown in FIGS. 2A and B. The cardiac phantom consisted of an input reservoir, pulsatile pump with a mixing chamber, myocardial perfusion volume, transit time flow probe and an output reservoir. The myocardial perfusion volume was placed inside an anthropomorphic chest phantom (Cardio; ORM, Mohrendorf, Germany). Water was circulated through the phantom using a pulsatile pump. Perfusion measurements were made for different flow rates using a 320-slice CT scanner (Aquilion One, Toshiba American Medical Systems, Tustin, Calif.) with a prospective cardiac perfusion protocol (320×0.5 mm collimation, 100 kVp and 200 mA). CT images were reconstructed from full projection data sets with a slice thickness of 0.5 mm using a medium-smooth FC03 kernel with standard beam hardening corrections. A total of 15 ml of contrast was injected at a rate of 5 mUs followed by a 15 ml water bolus at the same injection rate and prospective volume scans were acquired every cardiac cycle. CT images of the phantom, before and after contrast injection, are shown in FIG. 3. The center of the perfusion phantom is filled with contrast simulating the left ventricle. A large VOI encompassing the entire myocardial compartment was used for the tissue TAC, and another VOI approximately 2 $cm^2$ in cross-section and 0.3 cm thick was placed inside the artery to determine the AIF. FIG. 4 shows examples of an AIF and myocardial TAC showing the volume scans used for perfusion calculations. A threshold of 180 HU for the AIF was used to determine the first volume scan that will be used for perfusion measurement. The next five volume scans acquired over five consecutive cardiac cycles ($V_1$-$V_5$) were used for perfusion measurements. The first-pass analysis perfusion calculation was performed based on two ($V_1$ and $V_5$), three ($V_1$, $V_3$ and $V_5$), and five ($V_1$-$V_5$) volume scans. A number of small VOIs (0.3 cm³) in the myocardial compartment were also used for the maximum slope model perfusion measurements for comparison.

Figure 5:
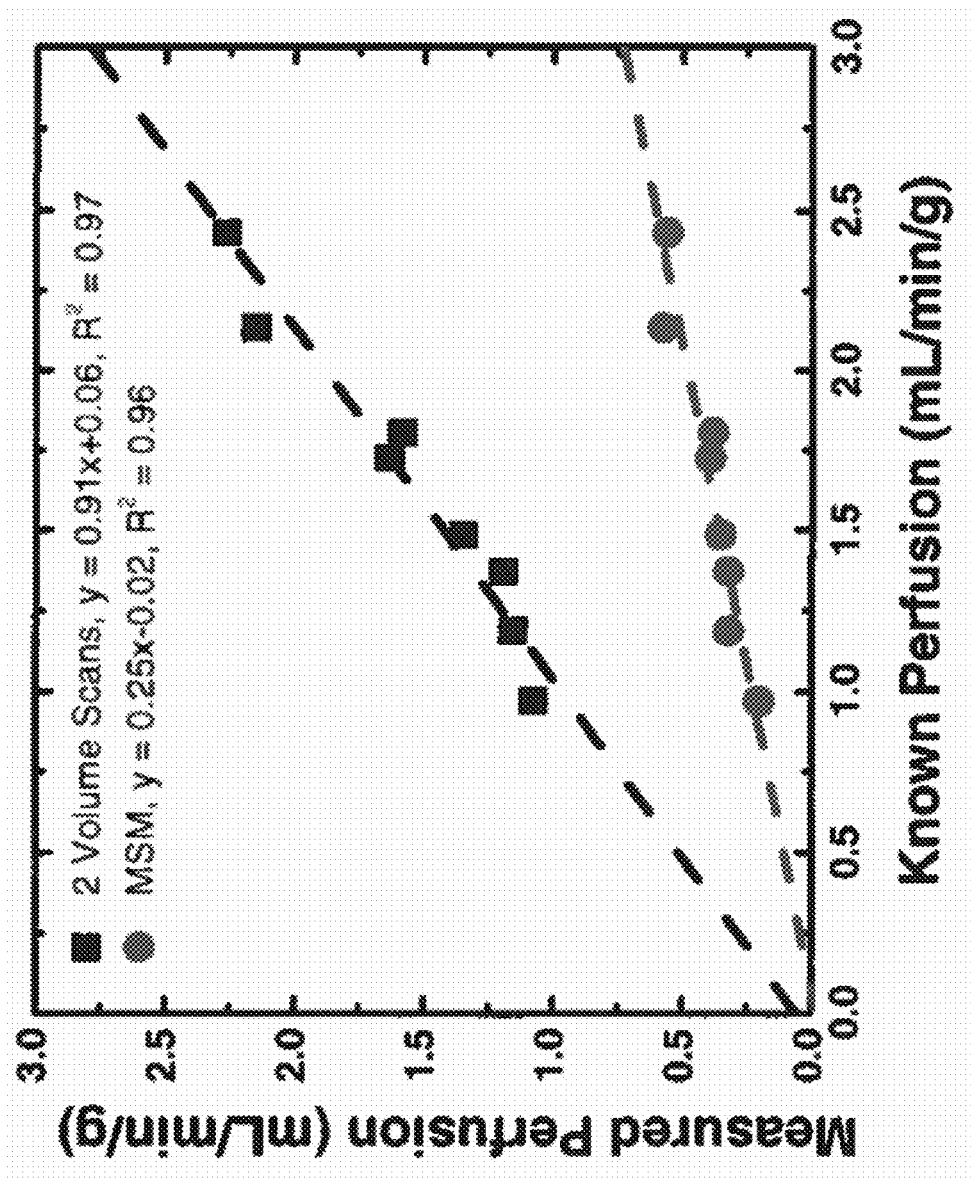
FIG. 5 illustrates the correlation of measured and known perfusion for the proposed technique using two volume scans along with the results from the maximum slope model (MSM).

FIG. 5 shows the correlation of measured and known perfusion for the disclosed technique using two volume scans along with the results from the maximum slope model (MSM). A summary of all the results is shown in Table 1. The results show an excellent correlation between the known and measured perfusion using 2, 3, and 5 volume scans with no significant difference between the results from 2 and 5 volume scans. On the other hand, the maximum slope model showed a significant systematic underestimation of the known perfusion. Furthermore, depending on the perfusion rate, the radiation dose for the maximum slope model was in the range of 11.7-17.5 mSv while the dose for the disclosed technique using two volume scans was 2.6 mSv. The results indicate that the disclosed technique can address the well-known systematic underestimation of the maximum slope model with a substantial reduction in radiation dose.

TABLE 1

| Method | Slope | Intercept | Pearson's r | SEE (mL/min/g) | Dose (mSv) |
|---|---|---|---|---|---|
| 2 Scans | 0.91 | 0.06 | 0.98 | 0.14 | 2.64 |
| 3 Scans | 0.91 | 0.06 | 0.98 | 0.14 | 3.96 |
| 5 Scans | 0.92 | 0.05 | 0.98 | 0.13 | 6.60 |
| MSM | 0.25 | −0.02 | 0.97 | 0.30 | 11.69-17.51 |

Example 2

Preliminary studies were performed using a swine animal model. Each swine was positioned on the CT (Aquilion One, Toshiba American Medical Systems, Tustin, Calif.) couch, and the couch was extended under a mobile C-arm for catheter placement. Standard procedures were used to place catheters in the femoral vein, femoral artery, left ventricle, and left main coronary artery. A pressure wire was advanced into the middle segment of the LAD coronary artery. An appropriately sized balloon catheter was positioned in the proximal LAD to induce varying degrees of stenosis. FFR was used to assess the severity of the induced stenosis. A coronary drip of adenosine (240 µg/min) was used to induce maximum hyperemia.

The animal was then positioned back in the CT gantry for image acquisition. CT acquisition was performed with a prospective ECG-gated cardiac perfusion protocol (320×0.5 mm collimation, 100 kVp and 200 mA). Volume scans (75% R-R interval) were acquired that contained the entire heart, for each cardiac cycle, over approximately 20 cardiac cycles, and reconstructed from full projection data sets with a slice thickness of 0.5 mm using a medium-smooth FC03 kernel with standard beam hardening (a) (b) (c) (d) corrections. This CT acquisition protocol enabled comparison between the disclosed technique and the MSM that requires the entire contrast pass curve to calculate perfusion. A total of 35 ml of contrast agent (370 mg/ml iodine) was injected at a rate of 7 mUsecond, followed by 35 ml of saline at the same rate for two swine (35-50 kg). CT images were acquired at maximum hyperemia. Fluorescent microspheres were injected into the apex of the left ventricle at each level of stenosis, and blood samples were taken at a known rate from the femoral artery. After each experiment, the heart was removed and 3-5 tissue samples were taken from the LAD, LCX, and RCA perfusion territories and sent out for independent florescence microspheres measurement (IMT Laboratories, Irvine, Calif.). The FFR measurements were used as a clinical reference standard, and fluorescent microspheres were used as a reference standard for absolute perfusion measurement and correlated with the results from different CT perfusion techniques.

Figure 11:
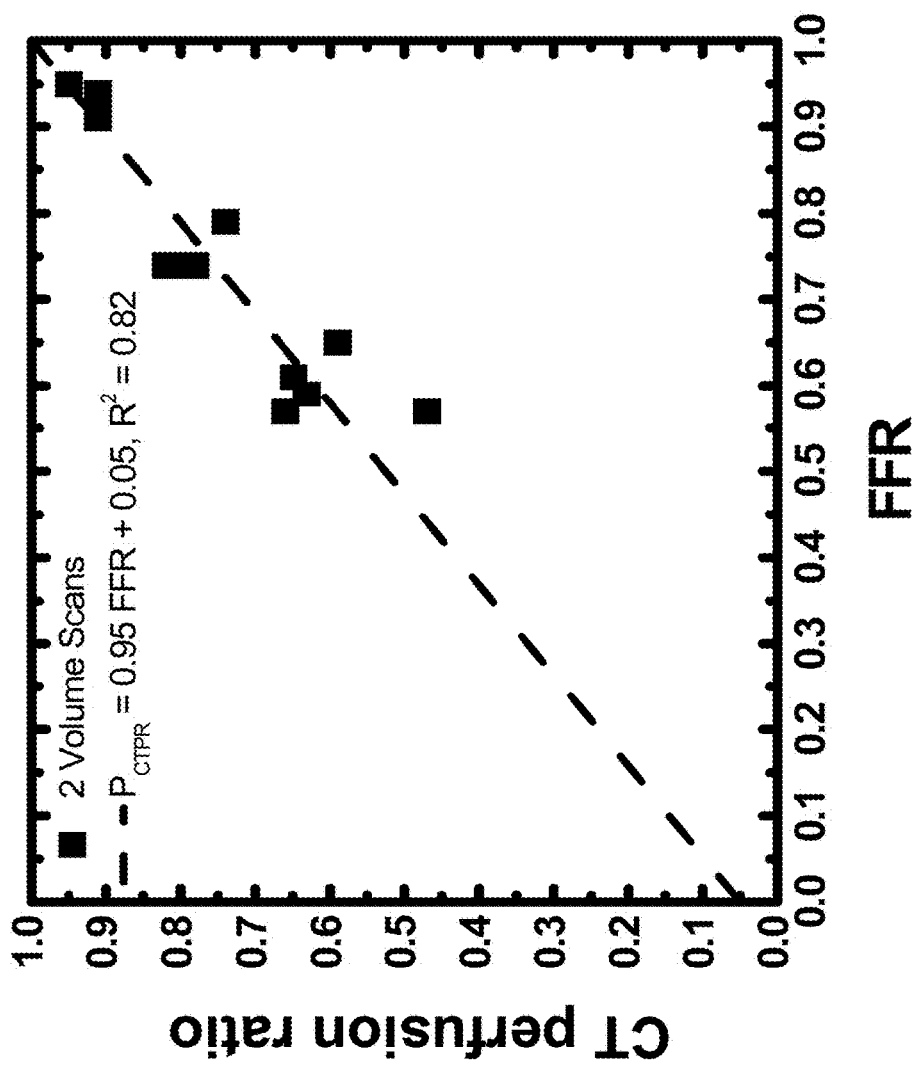
FIG. 11 illustrates the correlation of CT perfusion ratio and FFR for the proposed technique using two volume scans. The results show a correlation between the FFR measurements and CT perfusion ratios.
Figure 12:
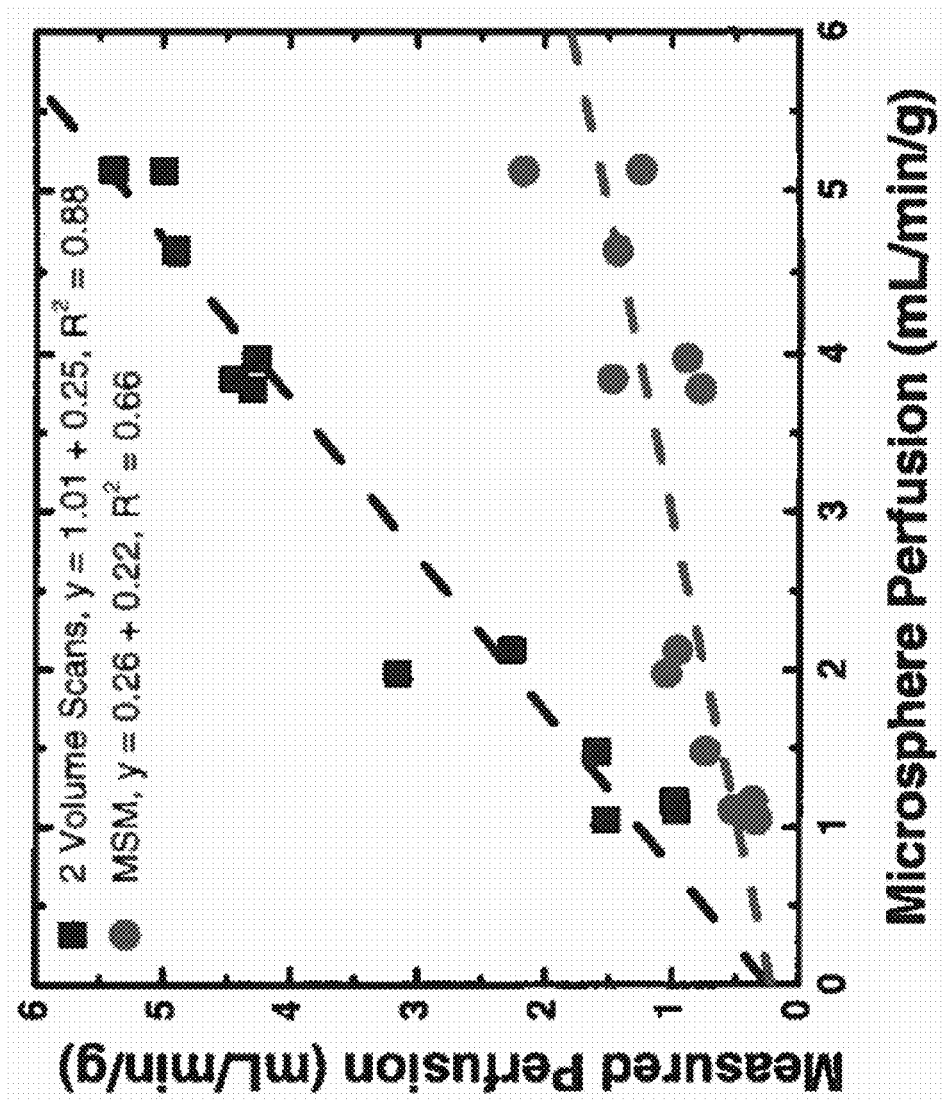
FIG. 12 illustrates the correlation of CT perfusion and microsphere perfusion for the proposed technique using two volume scans along with the results from the MSM.
Figures 13A, 13B, 13C:
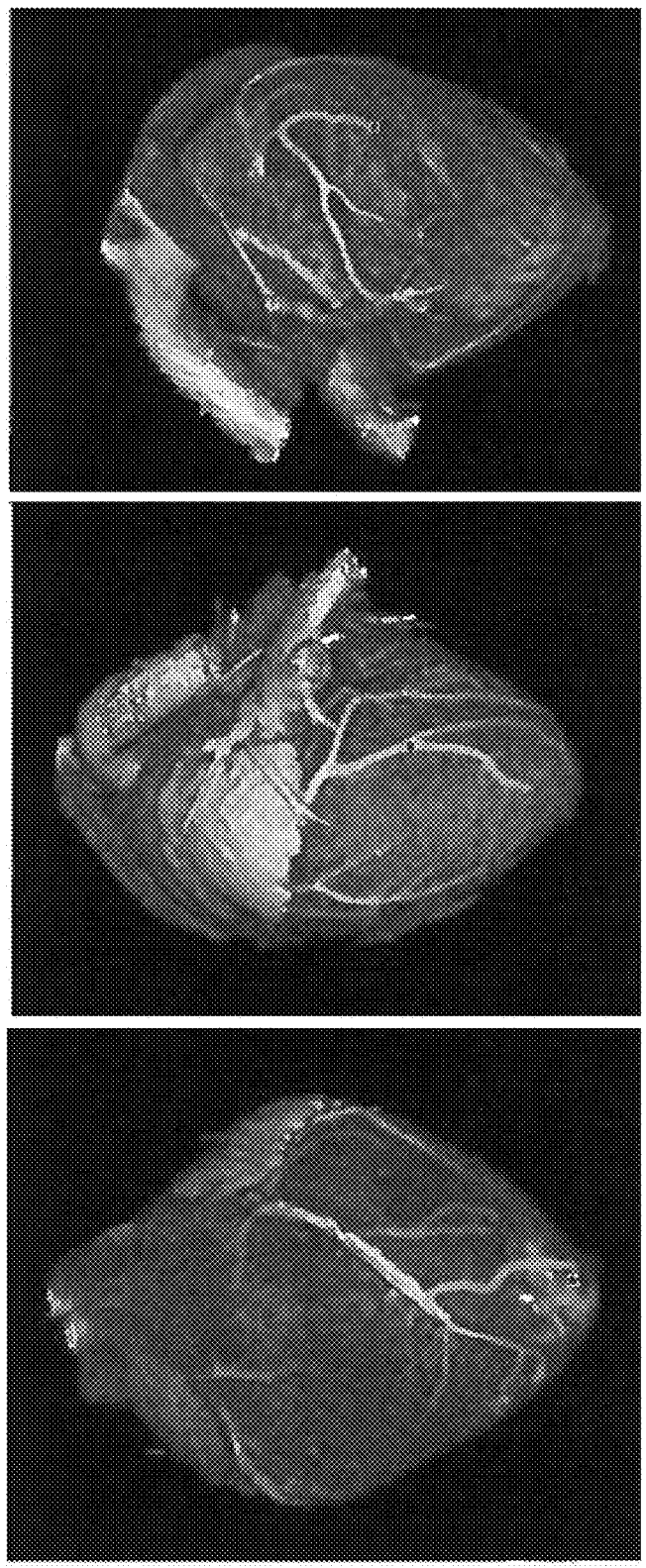
FIGS. 13A-13C illustrate 3D views of the heart generated through CT angiography.

The CT perfusion measurements were compared with both FFR and florescence microsphere measurements. CT perfusion ratio was calculated by dividing the LAD perfusion for different severity stenosis by the measured perfusion without any stenosis. The perfusion bed from a normal coronary artery could have been used for perfusion ratio measurement. However, the other perfusion beds were not at maximum hyperemia since an intracoronary drip of adenosine was used to produce maximum hyperemia in the LAD perfusion bed. FIG. 11 shows the correlation of CT perfusion ratio and FFR for the disclosed technique using two volume scans. The results show an excellent correlation between the FFR measurements and CT perfusion ratios. FIG. 12 shows the correlation of CT perfusion and microsphere perfusion for the disclosed technique using two volume scans along with the results from the MSM. A summary of all the results using 2-5 volume scans for perfusion calculation is shown in Table 2. The results show an excellent correlation between the microsphere measurements and perfusion measured using 2, 3, and 5 volume scans with no significant difference between the results from 2, 3 and 5 volume scans. On the other hand, similar to the phantom results, the maximum slope model showed a significant systematic underestimation of the microsphere perfusion. Furthermore, the radiation dose for the maximum slope model was 11.7-19.0 mSv while the dose for the disclosed technique using two volume scans was 2.6-2.9 mSv. The results indicate that the disclosed technique can address the well-known systematic underestimation of the MSM in addition to reducing radiation dose.

TABLE 2

Summary of the linear regression analysis between different CT perfusion methods and florescence microsphere measurements. The associated radiation dose is also included.

| Method | Slope | Intercept | Pearson's r | SEE (mL/min/g) | Dose (mSv) |
|---|---|---|---|---|---|
| 2 Scans | 1.01 | 0.25 | 0.97 | 0.08 | 2.64-2.88 |
| 3 Scans | 1.01 | 0.25 | 0.97 | 0.08 | 3.96-4.32 |
| 5 Scans | 0.89 | 0.47 | 0.94 | 0.10 | 6.60-7.20 |
| MSM | 0.26 | 0.22 | 0.81 | 0.06 | 11.69-19.00 |

Example 3

Figure 9:
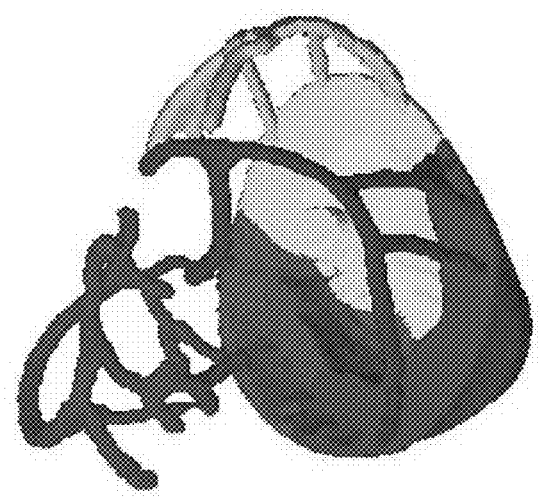
FIG. 9 illustrates a 3D representation of the extracted coronary arterial centerlines with assigned perfusion beds.

The disclosed perfusion bed assignment algorithm was evaluated by direct contrast injections into the LAD, LCX, and RCA arteries. The region of the myocardium with contrast was segmented on a slice-by-slice basis and compared with the assigned perfusion bed from the automated assignment algorithm. The average difference in the perfusion beds was calculated to be 5.2±4%, 6.7±4.1%, and 5.2±3.6% for the LAD, RCA, and LCX beds, respectively. FIG. 9 shows an example of the LAD perfusion bed enhancement and the assigned perfusion beds following direct contrast injection into the LAD of a swine.

What is claimed is:

1. A method of measuring regional organ perfusion with low radiation dose using whole-organ, wide-detector CT in a patient comprising:
    obtaining a first volume scan of a compartment of the organ at a first time;
    obtaining a second volume scan of the compartment of the organ at a second time; and
    measuring a perfusion volume of the compartment of the organ using a first-pass analysis method in conjunction with a conservation of mass measurement;
    wherein the perfusion volume measurement comprises determining the amount of iodinated blood entering the compartment within the interval between the first and second time.

2. The method of claim 1, wherein the conservation of mass measurement comprises determining the entire organ volume.

3. The method of claim 1, wherein the conservation of mass measurement comprises determining a sub-volume of the organ.

4. The method of claim 1, wherein the conservation of mass measurement can be modeled as a compartment comprising a unique organ entrance vessel and organ exit vessel.

5. The method of claim 1, wherein the perfusion volume measurement is determined within a single cardiac cycle.

6. The method of claim 1, further comprising applying the following formula:

$$P = \frac{Q}{M} = \frac{1}{MC_{ave}}\left(\frac{\Delta V}{\Delta t}\right)_{ave}$$

wherein P is the calculated perfusion (ml/min/g), Q is the calculated blood flow (ml/min), M is the tissue mass (g) calculated using the total volume of tissue in the compartment and the known physical density of tissue, $\Delta V/\Delta t$ is the rate of change in iodinated blood volume in the perfusion volume per unit time, and $C_{ave}$ is the average iodine concentration of the incoming blood at the time of measurement, derived from the arterial input for the compartment.

7. The method of claim 1, comprising calculating global perfusion by using the entire segmented myocardium as the perfusion volume of interest.

8. The method of claim 1, comprising calculating perfusion using a single perfusion volume of interest.

9. The method of claim 1, wherein the organ is at least one of: a heart, a brain, a lung, a kidney, and a liver.

10. The method of claim 1, further comprising obtaining a third volume scan at a third time,
    obtaining a fourth volume scan of the compartment of the organ at a fourth time; and
    wherein the perfusion volume measurement comprises determining the amount of iodinated blood entering the compartment within the interval between the third time, and the fourth time.

11. The method of claim 1, wherein CT angiography data is obtained simultaneously.

12. The method of claim 1, wherein the scan is performed using 0.5-5 mSv.

13. The method of claim 1, wherein the scan is performed using 2.5 mSv.

14. The method of claim 1, wherein the scan is performed using less than 5 mSv.

15. The method of claim 11, further comprising measuring vessel-specific perfusion by performing vessel centerline extraction and perfusion bed assignment.

16. The method of claim 10, wherein the third time corresponds to the contrast entering the organ from a second entrance vessel, and wherein the fourth time corresponds to the contrast being at its peak.

17. The method of claim 1, wherein the first time corresponds to the contrast entering the organ, and wherein the second time corresponds to the contrast being at its peak.

* * * * *